US012661459B2

(12) United States Patent
Kulkarni et al.

(10) Patent No.: US 12,661,459 B2
(45) Date of Patent: Jun. 23, 2026

(54) ADAPTOR FOR A MEDICAL CONTAINER, A MEDICAL CONTAINER COMPRISING SAID ADAPTOR, AND A METHOD FOR MANUFACTURING SAID ADAPTOR

(71) Applicant: Becton Dickinson France, Le Pont-de-Claix (FR)

(72) Inventors: Pooja Bhuvanesh Kulkarni, Pune (IN); Cédric Rivier, Voreppe (FR); Nicolas Euvrard, Durham, NC (US); Rajesh Poola, Chennai (IN); Julien Gagliano, Meylan (FR); Frédéric Michel, Rives (FR)

(73) Assignee: Becton Dickinson France, Le Pont-de-Claix (FR)

( * ) Notice: Subject to any disclaimer, the term of this patent is extended or adjusted under 35 U.S.C. 154(b) by 779 days.

(21) Appl. No.: 17/800,302

(22) PCT Filed: Feb. 17, 2021

(86) PCT No.: PCT/EP2021/053849
§ 371 (c)(1),
(2) Date: Aug. 17, 2022

(87) PCT Pub. No.: WO2021/165295
PCT Pub. Date: Aug. 26, 2021

(65) Prior Publication Data
US 2023/0063816 A1      Mar. 2, 2023

(30) Foreign Application Priority Data
Feb. 18, 2020    (EP) ..................................... 20305153

(51) Int. Cl.
*A61M 5/34* (2006.01)
*A61M 39/10* (2006.01)

(52) U.S. Cl.
CPC .............. *A61M 5/34* (2013.01); *A61M 39/10* (2013.01); *A61M 39/1011* (2013.01); *A61M 2039/1044* (2013.01)

(58) Field of Classification Search
CPC .................. A61M 5/344; A61M 5/345; A61M 2039/1044; A61M 2039/1077; A61M 2205/583
See application file for complete search history.

(56) References Cited

U.S. PATENT DOCUMENTS 4,507,113 A * 3/1985 Dunlap ................... A61M 5/30
604/71
5,454,409 A * 10/1995 McAffer ............... A61J 1/1425
141/330
(Continued)

FOREIGN PATENT DOCUMENTS

CA        2929473 C    6/2019
CN     102470222 A    5/2012
(Continued)

*Primary Examiner* — Kami A Bosworth
(74) *Attorney, Agent, or Firm* — The Webb Law Firm

(57)    ABSTRACT

The adaptor including a proximal part configured to be secured onto a distal tip of a medical container, a distal part configured to receive said connector in order to establish a fluid communication between the distal tip of the medical container and the connector, said distal part including a window extending through a lateral wall of the adaptor. The adaptor further includes an indicator that is movable between a first position and a second position wherein the indicator outwardly extends relative to the first position. This indicator includes blocking means configured to block a movement of the indicator 8 from said first position to the second position, and a cam portion configured to be pushed outwardly by the connector when the connector reaches a predetermined position in the adaptor, thereby unblocking and pushing the indicator to the second position in order to (Continued)

provide an end user with a visual and tactile indication that the connection between the connector and the adaptor is terminated.

14 Claims, 6 Drawing Sheets

(56) References Cited

U.S. PATENT DOCUMENTS

2015/0265500 A1\*  9/2015  Russo ................... A61M 5/322
                                                            604/239
2019/0083359 A1\*  3/2019  Knudsen ............... A61M 39/10
2019/0321564 A1\*  10/2019  Kim ...................... A61M 5/348

FOREIGN PATENT DOCUMENTS

| CN | 105013076 | A | 11/2015 |
|----|-----------|---|---------|
| CN | 109395242 | A | 3/2019 |
| CN | 209108087 | U | 7/2019 |
| EP | 3202390 | A1 | 8/2017 |
| EP | 3381502 | A1 | 10/2018 |
| ES | 2733321 | T3 | 11/2019 |
| WO | 2014099395 | A1 | 6/2014 |

\* cited by examiner

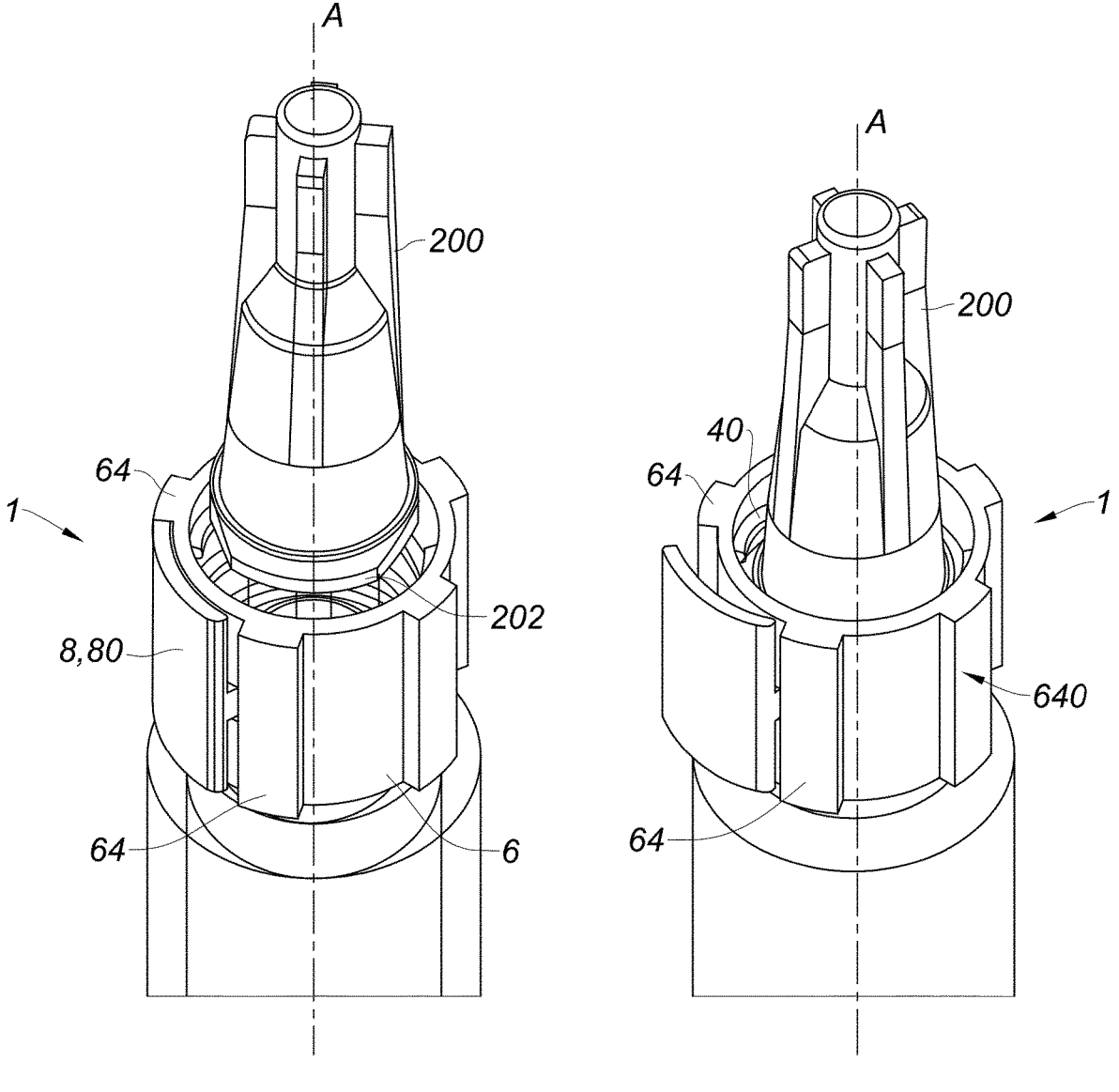
*Fig. 1* *Fig. 2*

ADAPTOR FOR A MEDICAL CONTAINER, A MEDICAL CONTAINER COMPRISING SAID ADAPTOR, AND A METHOD FOR MANUFACTURING SAID ADAPTOR

CROSS-REFERENCE TO RELATED APPLICATIONS

This application is the United States national phase of International Application No. PCT/EP2021/053849 filed Feb. 17, 2021, and claims priority to European Patent Application No. 20305153.7 filed Feb. 18, 2020, the disclosures of which are hereby incorporated by reference in their entirety.

BACKGROUND OF THE DISCLOSURE

Field of the Disclosure

The present disclosure relates to an adaptor for connecting a medical container to a connector, a medical container comprising said adaptor and a method for manufacturing said adaptor.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to an adaptor or a medical container of the invention, and the "proximal direction" is to be understood as meaning the opposite direction to said direction of injection, that is to say the direction towards the user's hand holding a medical container as for an injection operation.

Basically, medical containers, such as for example syringes, are preferably made of glass for its high chemical passivity, its low gas permeability and high transparency, which allows an extended storage and an easy inspection.

The medical container usually comprise a container forming a reservoir for containing a medical product. The container has a distal end in the form of a longitudinal tip defining an axial passageway through which the medical product is expelled from the container. However, this longitudinal tip does not allow parenteral administration by itself and must either comprise a staked needle or an adaptor allowing the connection of the syringe to a connector such as a needle hub. This connector is typically screwed into the adaptor and engages the distal end of the container to establish a fluid path between the reservoir and said connector.

Description of Related Art

It is important that the connector be properly screwed into the adaptor. The end user has to apply a sufficient torque when screwing the connector into the adaptor in order to get a proper fitting of the connector onto the distal end of the container. Under-screwing of the connector into the adaptor may otherwise lead to an ejection of the connector or a leakage when transferring a fluid between the container and the connector, the leakage occurring between the connector and the tip of the syringe. Alternatively, over-screwing of the connector into the adaptor may lead to the rotation or tilt of the adaptor.

There is therefore a need for a medical container providing the end user with an indication that the connector is properly screwed into the adaptor and thus improving the end user confidence during a connection and an injection step.

SUMMARY OF THE DISCLOSURE

An aspect of the disclosure is an adaptor for connecting a medical container to a connector, the adaptor comprising
a proximal part configured to be secured onto a distal tip of a medical container,
a distal part configured to receive said connector in order to establish a fluid communication between the distal tip of the medical container and the connector, said distal part comprising a window extending through a lateral wall of the adapter,
an indicator that is movable between a first position and a second position wherein the indicator outwardly extends relative to the first position, the indicator comprising blocking means configured to block a movement of the indicator from said first position to the second position, and
a cam portion protruding from the window inside the adaptor in the first position, said cam portion being configured to be pushed outwardly by the connector when the connector reaches a predetermined position in the adaptor, thereby unblocking and pushing the indicator to the second position in order to provide an end user with a visual indication that the connection between the connector and the adaptor is completed.

The adaptor of the invention thus permits the end user to know when the connection of the connector into the adaptor should stop in order to avoid an under- or over-fitted connection and therefore to avoid risks of leakage or of an ejection of the connector during a fluid transfer. Indeed, the indicator is arranged at a predetermined location on the adaptor, said location corresponding to the leakage limit. Therefore, the indicator is pushed in the second position only when the connector has reached this leakage limit. Furthermore, the blocking means prevent any inadvertent opening of the indicator prior to a secure connection of the connector in the adaptor, thus avoiding misleading the end user into thinking that the connection is completed. The cam portion that urges the indicator against the blocking means further provides an increasing screwing torque until the blocking means release the indicator that suddenly moves to the second position. This may consequently give an additional tactile indication that the connection is completed. Preferably, the indication that the connection is completed is both visual and tactile.

The first position may advantageously be such that a plane that is tangent to an external surface of the indicator and a plane that is tangent to an external wall of the adaptor may be equal to or lower than 5°, preferably equal to or lower than 2° and more preferably equal to about 0°.

The second position may advantageously be such that the plane tangent to an external surface of the indicator and the plane tangent to an external wall of the adaptor may be equal to or greater than 10°, preferably equal to or greater than 20°, more preferably equal to or greater than 30°.

The angle difference between the first and the second positions is advantageously equal to or greater than 10°, preferably equal to or greater than 20°, more preferably equal to or greater than 30°.

The adaptor of the disclosure preferably comprises an internal thread. Accordingly the connector is screwed to the adaptor. Advantageously, the connector comprises at least two wings which may be diametrally opposed to each other.

In an embodiment, the blocking means comprise a protrusion configured to abut against an inner surface of the adaptor lateral wall or against a grasping rib of the adaptor.

The cam portion may comprise a sloping wall configured to make the pressure exerted onto said cam portion by the connector progressively increase as the connector is screwed in the adaptor. This may provide a tactile indication to the end-user.

In an embodiment, the window opens in a thread root of an internal thread of the adaptor.

The cam portion may axially extend over the major part of the thread root width. This makes sure that the connecting element of the connector abuts against the cam portion whatever this connecting element is.

In an embodiment, the indicator is rotatably connected to the lateral wall of the adaptor.

Therefore, the indicator opens like a flap when the connection is secured.

The indicator may have a color that is different from the rest of the adaptor.

This enhances the visual indication provided to the end user.

The adaptor may be provided with an indicating surface that is hidden to the end-user in the first position and that is visible to the end-user in the second position, said indicating surface having a color that is different from the rest of the adaptor. This color difference improves the visual indication provided to the end user.

The indicator may have an external wall that axially extends over the window, preferably along the whole length of the adaptor. This long external wall makes the indicator readily visible to the end user, thus improving the visual indication.

In a first embodiment, the blocking means comprise a resilient leg configured to be deformed and then released when the indicator is pushed from the first position to the second position, thereby emitting a sound. For instance, said sound may be a "click".

In said first embodiment, the blocking means may alternatively or complementarily comprise a protrusion configured to abut against a grasping rib of the adaptor.

In the first embodiment, the indicator is attached on the adaptor, preferably clipped on the adaptor.

Accordingly, the indicator and the adaptor may be two distinct pieces that are assembled together. The indicator may comprise two bumps, or two recesses, and the window comprises two recesses, or two bumps, that are configured to receive said two bumps, or said recesses, so as to form a pivot connection.

In a second embodiment, the indicator and the adaptor are made of a single piece.

This limits the manufacturing costs and the number of manufacturing steps, since this embodiment does not require any assembly step.

In this second embodiment, the indicator is connected to the lateral wall by means of a resilient arm, said resilient arm being configured to stress the indicator towards the second position.

As a result, the indicator readily moves to the second position. Besides, this second position is more visible to a user since the resilient arm may be configured so that the indicator is substantially orthogonal to the adaptor lateral wall when the indicator reaches the second position.

In this second embodiment, the blocking means comprise a protrusion configured to abut against an inner surface of the adaptor lateral wall.

Another aspect of the disclosure is a medical container comprising a distal tip and the above-described adaptor, said adaptor being mounted onto the distal tip of the medical container.

In an embodiment, the medical container comprises a cap having a connecting portion engaged into the adaptor, said connecting portion being configured to secure the cap to the adaptor without abutting against the cam portion of the indicator.

Another aspect of the disclosure is a method for manufacturing the above-described adaptor, said method comprising the steps of:

forming the indicator by injection molding;

forming the adaptor by injection molding.

In an embodiment, the method further comprises the step of assembling the indicator and the adaptor.

In an alternative embodiment, the steps of forming the indicator and forming the adaptor are a single step of forming the indicator and the adaptor altogether in the same injection mold.

In said embodiment, the indicator is injection molded so as to be in the second position.

As a result, the normal shape of the indicator is when the indicator is in the second position. The first position thus corresponds to an unstable position: the indicator tends to return to the second position and is only prevented to do so by the blocking means, until the pressure exerted by the connector onto the cam portion overcomes the action of the blocking means, thereby leaving the indicator free to return to normal shape, i.e. to move to the second position.

BRIEF DESCRIPTION OF THE DRAWINGS

The disclosure and the advantages arising therefrom will clearly emerge from the detailed description that is given below with reference to the appended drawings as follows:

FIG. 1 is a perspective view of an adaptor according to a first embodiment of the invention, wherein the indicator is in the first position, FIG. 2 is a perspective view of an adaptor according to the first embodiment of the invention, wherein the indicator is in the second position.

DETAILED DESCRIPTION

Figure 3:
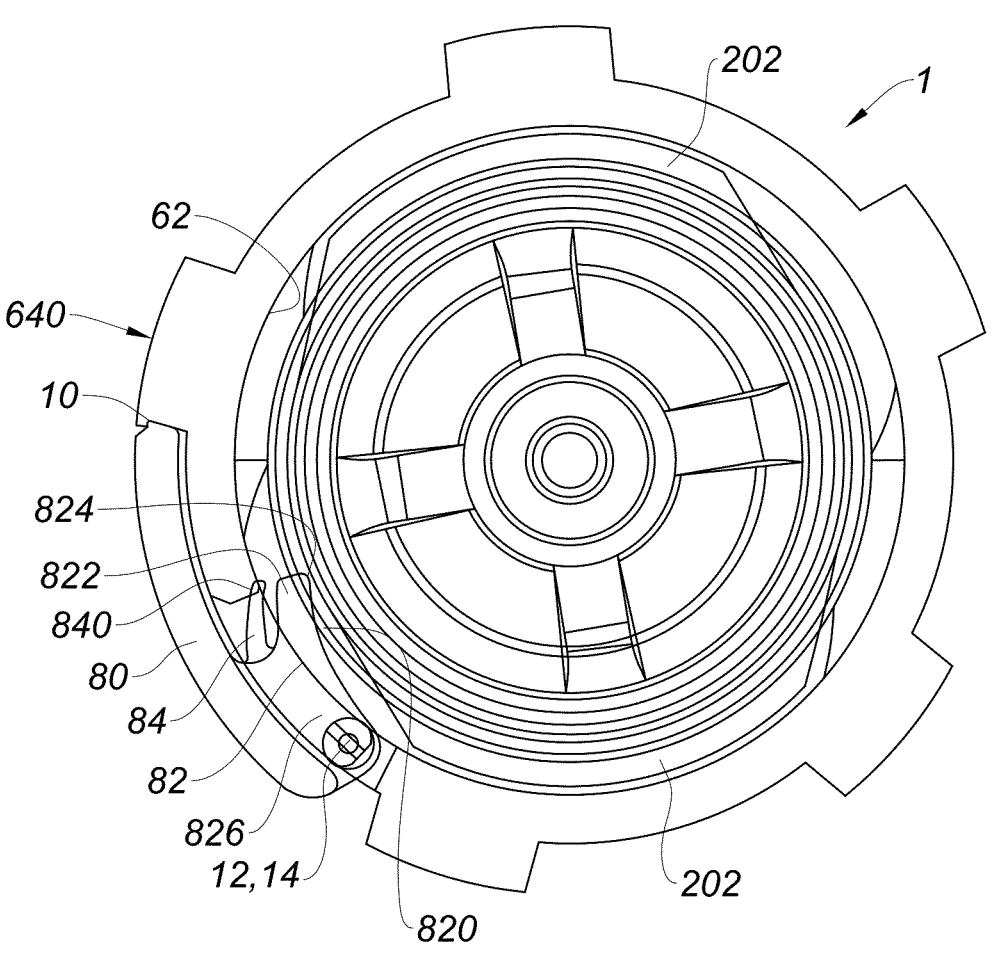
FIG. 3 is a top view of an adaptor according to the first embodiment of the invention, wherein the indicator is in the first position.

With reference to FIG. 1 is shown an adaptor 1 according to an embodiment of the disclosure. With reference to FIG.

8, the adaptor 1 is intended to be mounted onto a distal tip 102 of a medical container 100, more precisely onto an outer surface of said distal tip 102. The outer surface may be either cylindrical or distally tapered. The adaptor 1 permits to connect a connector, such as a needle hub 200, to this distal tip 102.

The adaptor 1 comprises a proximal part 2, which may be in the form of a mounting ring, configured to be secured to the medical container 100, and a distal part 4, which may be in the form of a connecting ring, configured to receive the connector in order to establish a reliable fluid communication between a passageway of the distal tip 102 and said connector. The distal part 4 thus includes connecting means, such as an internal thread 40, configured to engage corresponding connecting means, such as wings 202 of the needle hub 200, in order to secure the connector to the distal tip 102. Advantageously, the connector such as the needle hub 200 received in the adaptor 1 comprises two wings 202, diametrally opposed. As shown on FIG. 8, the internal thread 40 has a thread crest 40a and a thread root 40b. The connecting means may alternatively comprise a bayonet element, a snapping element or a press-fit element.

Figure 9:
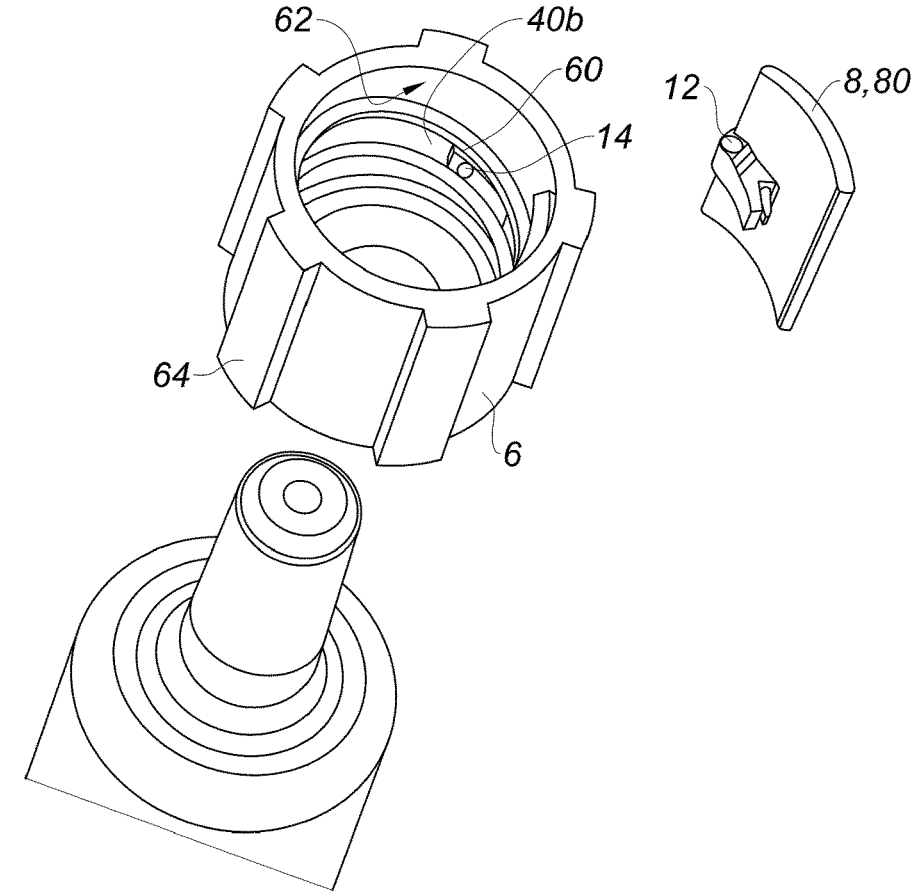
FIG. 9 is an exploded view of an adaptor according to the first embodiment of the invention.
Figure 10:
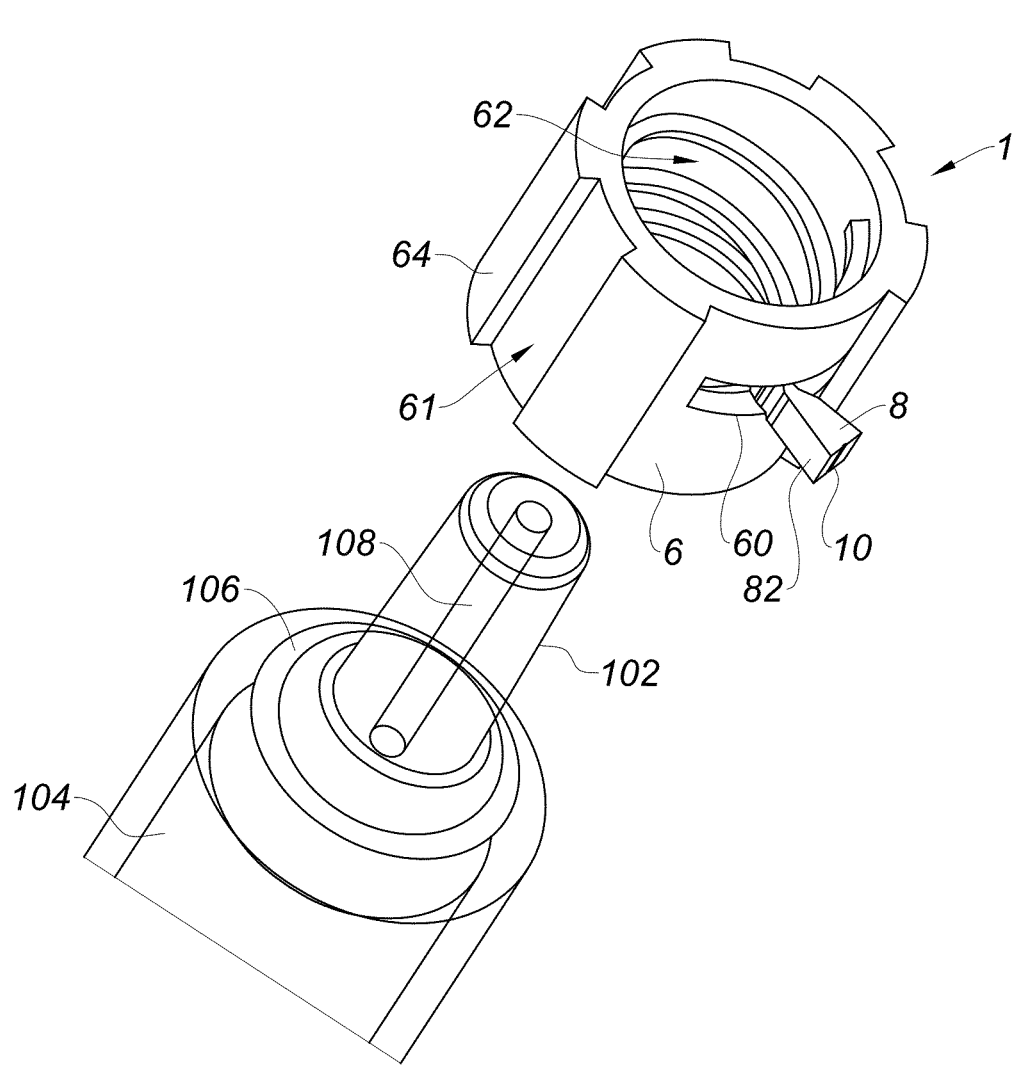
FIG. 10 is an exploded view of an adaptor according to the second embodiment of the invention.

With reference to FIGS. 9 and 10, the adaptor 1 has a lateral wall 6 that is provided with a window 60. The window 60 defines a through-opening extending from an outer surface to an inner surface 62 of said lateral wall 6. The window 60 may be arranged along the path of the connecting means of the connector. As shown on FIG. 9, the window 60 may preferably open in the thread root 40b of the internal thread 40. The window 60 might however open in another location of the adaptor 1, such as the thread crest 40a of the the internal thread 40. The window 60 may longitudinally extend parallel to the internal thread 40, i.e. define an angle with a longitudinal axis A of the adaptor 1 or with a transversal plane orthogonal to said longitudinal axis A. The lateral wall 6 of the adaptor 1 may include axial grasping ribs 64. The window 60 may be located through a portion of the lateral wall 6 that is located between two adjacent grasping ribs 64.

The adaptor 1 further comprises an indicator 8 configured to indicate to the end user that the connection between the connector and the adaptor 1 is completed. Specifically, the indicator 8 is movable between a first position (FIGS. 1, 3-5, 7) wherein the indicator 8 is against or close to the lateral wall 6 of the adaptor 1 and a second position (FIGS. 2, 6, 10) wherein the indicator 8 outwardly extends from the first position. In the first position, the indicator 8 may extend through the window 60. The first position of the indicator 8 relative to the adaptor 1 may be such that a plane that is tangent to an external surface of the indicator 8 and a plane that is tangent to an external wall of the adaptor 1 may be equal to or lower than 5°, preferably equal to or lower than 2° and more preferably equal to about 0°. The second position of the indicator 8 relative to the adaptor 1 may be such that the plane tangent to an external surface of the indicator 8 and the plane tangent to an external wall of the adaptor 1 may be equal to or greater than 10°. Preferably, the angle difference between the first and the second positions is advantageously equal to or greater than 10°, preferably equal to or greater than 20°, more preferably equal to or greater than 30°, so that the end user can easily notice that the connection is completed.

The adaptor 1 comprises blocking means, as will be described in further details below, configured to retain the indicator 8 in the first position as long as the connection between the connector and the adaptor 1 is not completed.

Figure 7:
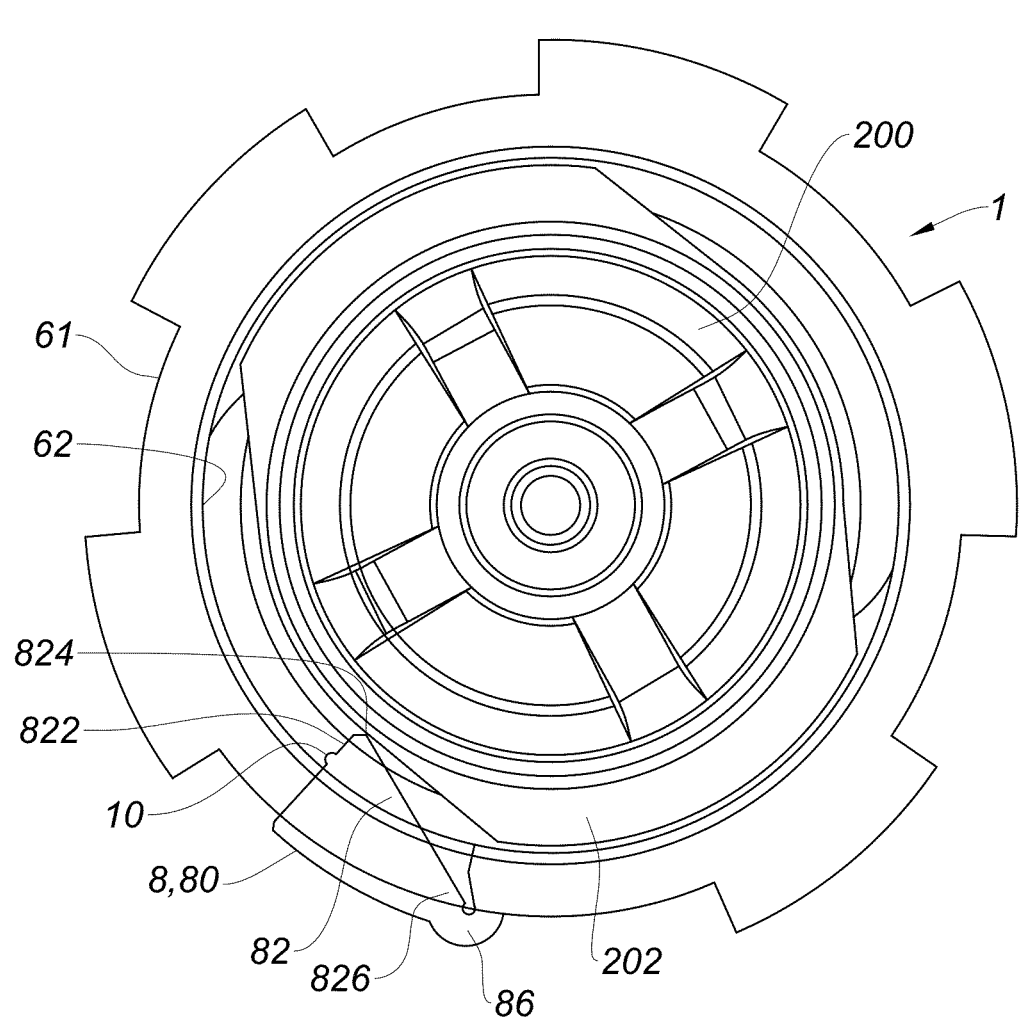
FIG. 7 is a top view of an adaptor according to the second embodiment of the invention, wherein the indicator is in the first position.

As shown on FIGS. 3 and 7, the indicator 8 further comprises a cam portion 82 that extends through the window 60 in the first position. The cam portion 82 is configured to be pushed outwardly by the connector, preferably radially outwardly, when the connector reaches a predetermined position in the adaptor 1, thereby causing the insertion of the connector into the adaptor 1 to overcome the action of the blocking means and to push the indicator 8 to the second position. Said predetermined position is advantageously defined as being the leakage limit of the connector as defined in the ISO 80369-7 (2016) (paragraphs 6.1 and 6.2). Whether the connector is under connected and has not reach said position, a leakage may occur. On the contrary, if the connector has been over connected, the connector may be broken or ejected from the adaptor. It should be noted that the indicator 8 is configured to be activated, i.e. moved to the second position, only when the connector reaches the leakage limit position. The indicator 8, more specifically the cam portion 82 of the indicator 8, is therefore located on the adaptor 1 such that the indicator 8 moves to the second position only when the connector reaches the predetermined position.

As visible on FIGS. 3 and 7, the cam portion 82 inwardly protrudes from an inner 62 face of the lateral wall 6 of the adaptor 1 in the first position. The cam portion 82 is arranged on the path of the connector, more specifically on the path of the connecting means of the connector. With reference for example to FIG. 9, the cam portion 82 is advantageously located in the thread root 40b of the inner thread in the first position. It is contemplated that the cam portion 82 may axially extend over the major part of the thread root 40b width so as to make sure that the wings 202 of the needle hub 200 abut against the cam portion 82 of the indicator 8 when the connector reaches the predetermined position. The cam portion 82 may comprise a sloping wall 820 configured to make the pressure exerted onto said cam portion 82 by the connector progressively increase as the connector is screwed in the adaptor 1. This sloping wall 820 may have a planar or concave abutment surface. The action of the cam portion 82 and the blocking means creates an increase followed by a release in the screwing torque, thereby providing the user with a further tactile indication that the connection is completed. The sloping wall 820 is shaped so that the cam portion 82 is pushed outwardly by the connector, preferably radially outwardly or alternatively in another direction such as axially outwardly.

In the first embodiment, with reference to FIG. 3, the indicator 8 comprises sound-emitting means such as a resilient leg 84 configured to emit an audible sound when the indicator 8 moves from the first position to the second position, thereby providing the end user with an audible indication that the connection is completed. The resilient leg 84 may be configured to be deformed and then released when the indicator 8 is pushed from the first position to the second position so that the resilient leg 84 emits a sound, preferably a click. The resilient leg 84 may extend between the cam portion 82 and an external wall 80 of the indicator 8. The resilient leg 84 may have a free end 840 configured to abut against the lateral wall 6 of the adaptor 1 in the first position, to deform when the connector abuts against the cam portion 82, and to return to normal shape when the indicator 8 moves to the second position. In an embodiment, the blocking means comprise said resilient leg 84. The resilient leg 84 may be curved inwardly in normal shape, i.e. in a non-deformed condition.

In the first embodiment illustrated on FIG. 3, the blocking means may alternatively or complementarily comprise a protrusion 10 configured to abut against against a grasping rib 64. The protrusion 10 may be an axially extending rib or shoulder. The protrusion 10 may have a rounded shape. As shown on FIG. 3, the protrusion 10 may be located on the external wall 80 of the indicator 8, for example at an edge thereof.

In the first embodiment illustrated on FIGS. 1-3 and 9, the indicator 8 may have an external wall 80 that may close the window 60 in the first position and may open the window 60 in the second position. The external wall 80 possibly extends parallel to the lateral wall 6 of the adaptor 1 in the first position and may be angled or orthogonal to said lateral wall 6 in the second position. The external wall 80 may be flush with the lateral wall 6 or an outer surface 640 of the grasping ribs 64 in the first position, so that the indicator 8 advantageously does not protrude from the lateral wall 6 of the adaptor 1 in said first position. As shown on FIGS. 1, 2 and 9, the external wall 80 of the adaptor 1 is preferably greater than the window 60 and may axially extend over a major part of the adaptor 1 length, preferably along the whole length of the adaptor 1, as visible on FIGS. 1 and 2. This feature enables to have a better visual indication whether the indicator 8 is in the first or second position.

In the second embodiment illustrated on FIG. 7, the blocking means may comprise a protrusion 10 configured to abut against an inner surface 62 of the lateral wall 6. The protrusion 10 may be an axial rib. The protrusion 10 may have a rounded shape. As shown on FIG. 7, the protrusion 10 may be located on the cam portion 82 of the indicator 8, more specifically at a second end 822 of the cam portion 82.

The indicator 8 is rotatably mounted onto the adaptor 1, around a rotation axis that may be parallel or orthogonal to the longitudinal axis A of the adaptor 1. Preferably, the indicator 8 is rotatably mounted onto the adaptor 1, around a rotation axis that is parallel to the longitudinal axis A of the adaptor 1. Accordingly the cam portion 82 is preferably configured to be pushed radially outwardly by the connector when the connector reaches the predetermined position in the adaptor 1. The adaptor 1 comprises a pivot connection that rotatably connects the indicator 8 to the lateral wall 6 of the adaptor 1. The indicator 8 thus forms a rotatable flap that closes the window 60 in the first position and that opens the window 60 in the second position. As shown on FIG. 3 or 7, the rotation axis may be located at a first end 826 of the cam portion 82, and said cam portion 82 may have an apex 824 provided at a second end 822 opposing said first end 826. The adaptor 1 may include biasing means configured to bias the indicator 8 towards the second open position, so that the indicator 8 suddenly pops out to the second position when the connection is completed. As a result, the indicator 8 in the second position may be in a stable equilibrium condition, whereas the indicator 8 in the first position may be in an unstable equilibrium condition.

In the first embodiment illustrated on FIGS. 1 to 3 and 9, the indicator 8 and the adaptor 1 are two distinct pieces that are assembled together. The pivot connection may be formed by two bumps 12 engaged with two complementarily shaped recesses 14. The bumps 12, or the recesses, may be arranged on the indicator 8, whereas the recesses 14, or respectively the bumps, are arranged in the window 60.

Figures 4, 5, 6:
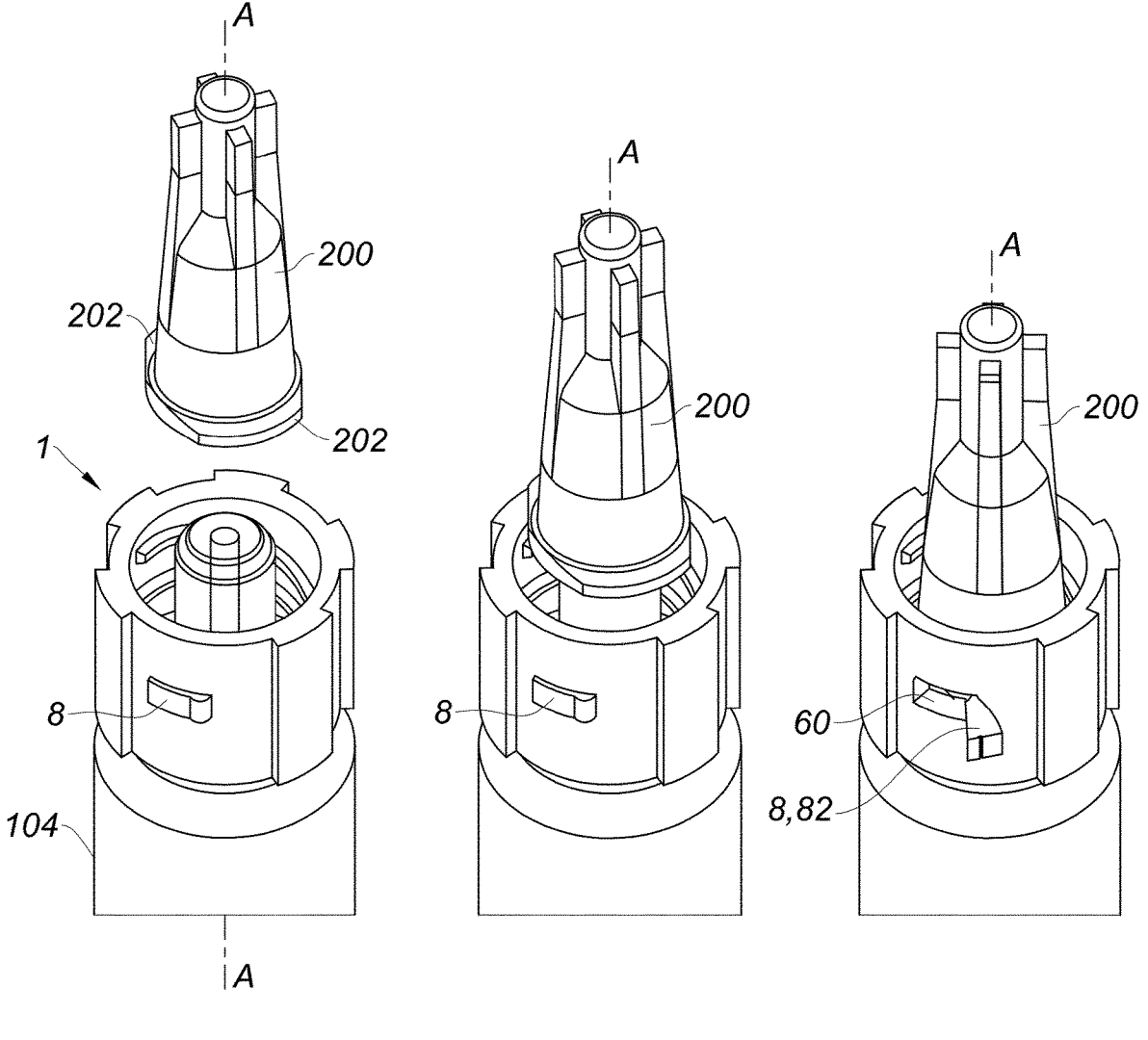
FIG. 4 is a perspective view of an adaptor according to a second embodiment of the invention, wherein the indicator is in the first position.
FIG. 5 is a perspective view of an adaptor according to the second embodiment of the invention, wherein the indicator is in the first position.
FIG. 6 is a perspective view of an adaptor according to the second embodiment of the invention, wherein the indicator is in the second position.

In the second embodiment illustrated on FIGS. 6-7 and 10, the indicator 8 and the adaptor 1 are molded in a single piece. The connection may be formed by a resilient arm 86 connecting the indicator 8 to the lateral wall 6 of the adaptor 1, more specifically into the window 60. The resilient arm 86 may form the biasing means that bias the indicator 8 towards the second open position.

It is contemplated that the indicator 8 advantageously has a color that is different from the rest of the adaptor 1 and more specifically different from a color of the lateral wall 6 of the adaptor 1. It is also possible that the adaptor 1 be provided with an indicating surface that is hidden to the end user when the indicator 8 is in the first position and that becomes visible to the end user when the indicator 8 is in the second position. This indicating surface may have a color that is different from the rest of the adaptor 1 and more specifically from any surface that is visible to the end user when the indicator 8 is in the first position. For example, the indicating surface may be an inner surface 80a of the external wall 80 of the indicator 8, or an edge surface 8a of the indicator 8, or an outer surface 61 of the lateral wall 6, said outer surface 61 being hidden by the indicator 8 in the first position.

The adaptor 1 may be made of a plastic material, more precisely of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. Preferably, the adaptor 1 is made of polycarbonate (PC). The indicator 8 may be made of the same material as the rest of the adaptor 1, or of a different material among for example high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. In the first embodiment shown on FIGS. 1 to 3 and 9, the indicator may preferably be made of polycarbonate (PC). In the second embodiment shown on FIGS. 4-7 and 10, the indicator may preferably be made of polypropylene (PP) or polyoxymethylene (POM).

Figure 8:
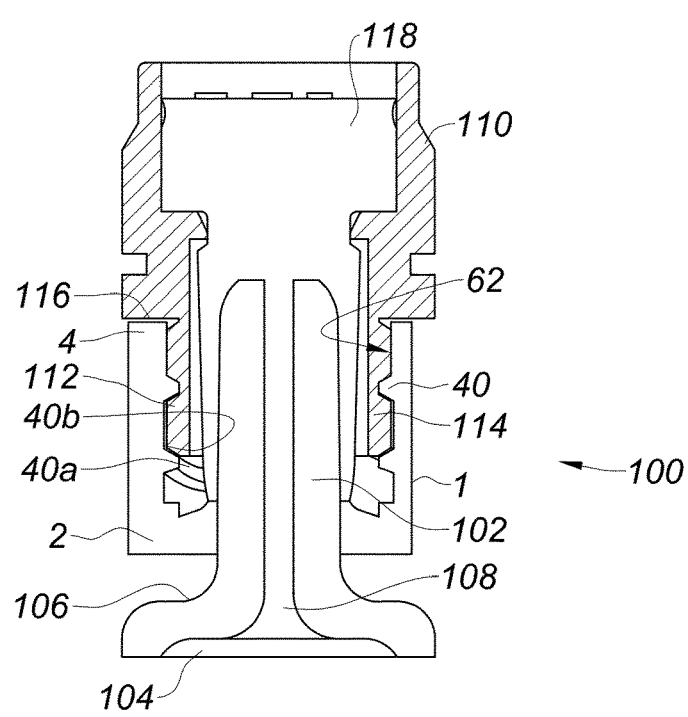
FIG. 8 is a cross-section view of a medical container according to an embodiment of the invention.

With reference to FIGS. 8-10, the invention also relates to a medical container 100 comprising a distal tip 102 and an adaptor 1 having the above-described features, said adaptor 1 being mounted onto the distal tip 102 of the medical container 100. The medical container 100, which may be a syringe, such as pre-fillable or prefilled syringe, comprises a tubular barrel 104 that defines a reservoir for a medical product. The tubular barrel 104 is provided with the distal tip 102 that may protrude from a distal shoulder 106. The distal tip 102 may be cylindrical or distally tapered. The distal tip 102 includes an internal passageway 108 in communication with the reservoir. The tubular barrel 104 and the distal tip 102 are preferably made of glass. The medical container 100 may be provided with a piston and a plunger rod (not shown) so as to expel the medical product from the reservoir and through the passageway. The adaptor 1 may secured to the distal tip 102 by gluing, screwing, friction force or snap fitting.

With reference to FIG. 8, the medical container 100 may comprise a cap 110 having an external thread 112 configured to engage the internal thread 40 of the adaptor 1 so as to secure the cap to the adaptor 1. The cap 110 is configured to be secured to the adaptor 1 without its external thread 112 abutting the cam portion 82 of the indicator 8. Therefore, the cap 110 may include a connecting portion 114 whose length is less than a distance between the distal end of the adaptor 1 and the cam portion 82 of the indicator 8. Besides, the cap 110 may comprise a proximal abutment surface 116 configured to abut against the distal end of the adaptor 1 so that the cap 110 cannot be inserted further into the adaptor 1, thereby preventing the cap 110 from exerting any pressure onto the cam portion 82. The cap 110 may include an inner cap 118, which may be made of a softer material than the cap, so as to sealingly close the distal tip 102.

The use of the adaptor 1 is described herein below with reference to FIG. 1-2 or 4-6.

The user inserts the connector into the distal end of the adaptor 1 and engages the wings 202 of the needle hub 200 with the internal thread 40 of the adaptor 1. The user starts screwing the needle hub 200 into the adaptor 1. Once the needle hub 200 reaches the predetermined position, the wings 202 of the needle hub 200 start abutting against the cam portion 82 of the indicator 8, said wings 202 applying a radial pressure on this cam portion 82. However, due to the blocking means, the indicator 8 remains in the first position and does not open as long as the radial force exerted by the needle hub 200 on the cam portion 82 is not high enough. The user goes on screwing the needle hub 200 into the adaptor 1. The radial force exerted by the needle hub 200 thus increases until this force overcomes the action of the blocking means. The indicator 8 is thus moved towards the second position, making it visible to the end user that the needle hub 200 has reached the predetermined position. Thus, the connection is completed (FIGS. 2 and 6). In this position, the connection between the needle hub 200 and the adaptor 1 is strong enough to allow the user to perform an injection operation without risk of leakage. This position also deters any over-screwing that would lead the user to apply a too high screwing torque and that would accordingly cause the adaptor 1 to rotate relative to the distal tip 102, and/or would lead to a break of the needle hub 200 and/or adaptor 1.

The disclosure also relates to a method for manufacturing the above-described adaptor 1, said method comprising the steps of:

forming the indicator 8 by injection molding;
forming the adaptor 1 by injection molding.

With reference to the adaptor 1 according to the first embodiment shown on FIGS. 1-3 and 9, the method may further comprise the step of assembling the indicator 8 and the lateral wall 6 of the adaptor 1. For example the indicator 8 is clipped in the lateral wall 6 of the adaptor 1. More specifically, the bumps of the indicator 8 are positioned into the recesses of the window 60. The indicator 8 is thus rotatably mounted onto the adaptor 1 in a single, simple step.

With reference to the adaptor 1 according to the second embodiment shown on FIGS. 4-7 and 10, the steps of forming the indicator 8 and forming the adaptor 1 are a single step of forming the indicator 8 and the rest of the adaptor 1 in the same injection mold. The adaptor 1 and the indicator 8 may thus be of the same material, or may be co-injection molded so as to be made of two different materials. In this case, the material of the indicator 8 may be less rigid than the material forming the rest of the adaptor 1. Preferably, the indicator 8 and the adaptor 1 are injection molded altogether with the indicator 8 being in the second position, so that the normal shape of the indicator 8 is the second open position. In this second position the resilient arm 86 is not deformed. The method comprises a further step of moving the indicator 8 in the first position until the blocking means are activated and thus maintain the indicator 8 in the first position against the spring action of the deformed resilient arm 86.

The invention claimed is:

1. An adaptor for connecting a medical container to a connector, the adaptor comprising:

a proximal part configured to be secured onto a distal tip of the medical container, a distal part configured to receive said connector in order to establish a fluid communication between the distal tip of the medical container and the connector, said distal part comprising a window extending through a lateral wall of the adaptor, and an indicator that is movable between a first position and a second position wherein the indicator outwardly extends relative to the first position, the indicator comprising:

blocking means configured to block a movement of the indicator from said first position to the second position, and a cam portion protruding from the window inside the adaptor in the first position, said cam portion being configured to be pushed outwardly from the window by the connector when the connector reaches a predetermined position in the adaptor, thereby unblocking and pushing the indicator to the second position in order to provide an end user with a visual indication that the connection between the connector and the adaptor is completed, wherein the blocking means comprise a protrusion or a resilient leg for abutting against another part of the adaptor to block the indicator in the first position.

2. The adaptor according to claim 1, wherein the protrusion is configured to abut against an inner surface of the lateral wall or against a grasping rib of the adaptor.

3. The adaptor according to claim 1, wherein the window opens in a thread root of an internal thread of the adaptor.

4. The adaptor according to claim 1, wherein the indicator is rotatably connected to the lateral wall of the adaptor.

5. The adaptor according to claim 1, wherein the resilient leg is configured to be deformed and then released when the indicator is pushed from the first position to the second position, thereby emitting a sound.

6. The adaptor according to claim 1, wherein the indicator is attached on the rest of the adaptor.

7. The adaptor according to claim 1, wherein the indicator and the rest of the adaptor are made of a single piece.

8. The adaptor according to claim 1, wherein the indicator is connected to the lateral wall by means of a resilient arm, said resilient arm being configured to stress the indicator towards the second position.

9. A medical container comprising a distal tip and the adaptor according to claim 1, said adaptor being mounted onto the distal tip of the medical container.

10. The medical container according to claim 9, wherein the medical container comprises a cap having a connecting portion engaged into the adaptor, said connecting portion being configured to secure the cap to the adaptor without abutting against the cam portion of the indicator.

11. A method for manufacturing the adaptor according to claim 1, said method comprising the steps of:

forming the indicator by injection molding; and
forming the rest of the adaptor by injection molding.

12. The method according to claim 11, wherein the method further comprises the step of assembling the indicator and the rest of the adaptor.

13. The method according to claim 11, wherein the indicator and the rest of the adaptor are formed altogether in the same injection mold.

14. The method according to claim 13, wherein the indicator is injection molded so as to be in the second position.

* * * * *